United States Patent

Kaiho et al.

[11] Patent Number: 5,499,532
[45] Date of Patent: Mar. 19, 1996

[54] AQUAMETER

[75] Inventors: Mamoru Kaiho, Toride; Hajime Yasuda, Tsukuba, both of Japan

[73] Assignee: Director-General Of Agency Of Industrial Science And Technology, Japan

[21] Appl. No.: 214,565

[22] Filed: Mar. 18, 1994

[30] Foreign Application Priority Data

May 18, 1993 [JP] Japan .................... 5-139613

[51] Int. Cl.⁶ .................... G01N 5/04; G01N 25/56
[52] U.S. Cl. .................... 73/76; 374/14
[58] Field of Search .................... 73/76, 73; 374/14

[56] References Cited

U.S. PATENT DOCUMENTS

| | | | |
|---|---|---|---|
| 2,017,376 | 10/1935 | Rother et al. | 73/73 |
| 2,816,437 | 12/1957 | Hornberger et al. | 73/76 |
| 4,291,775 | 9/1981 | Collins | 374/14 |
| 4,615,405 | 10/1986 | Morino et al. | 374/14 X |
| 4,964,734 | 10/1990 | Yoshida et al. | 374/14 |

FOREIGN PATENT DOCUMENTS

| | | | |
|---|---|---|---|
| 59645 | 2/1990 | Japan | 73/73 |
| 134541 | 6/1991 | Japan | 73/73 |
| 3255334 | 11/1991 | Japan | 73/73 |
| 718444 | 11/1954 | United Kingdom | 73/76 |
| 2202054 | 9/1988 | United Kingdom | 73/73 |

Primary Examiner—William A. Cuchlinski, Jr.
Assistant Examiner—Willie Morris Worth
Attorney, Agent, or Firm—Lorusso & Loud

[57] ABSTRACT

A device for measuring the moisture content of a moisture-containing sample, which includes an electronic balance for measuring the weight of an airtight sample holder containing the sample and placed on a receiver thereof. The sample holder has a side wall provided with a gas discharge pipe extending horizontally outwardly from therefrom. A gas feed tube having a front portion inserted into the gas discharge pipe of the sample holder is held without contacting with the inside wall of the discharge pipe. An infrared lamp is disposed above the electronic balance to heat the sample in the sample holder and to remove the moisture from the sample. By feeding an inert gas through the feed tube into the sample holder, the heating of the sample with the lamp is performed in an inert gas atmosphere.

4 Claims, 3 Drawing Sheets

AQUAMETER

BACKGROUND OF THE INVENTION

1. Field of the Invention:

This invention relates to a device for measuring the water content of a substance.

2. Description of the Prior Art:

It is well known to measure the moisture content of a substance by heating the substance placed on an electronic balance to remove the moisture therefrom. The change in weight of the substance is continuously measured and indicated by the balance throughout the drying. This method is thus advantageous because quick, precise measurement of the moisture content is attainable. However, with known aquameters designed to perform the above-mentioned technique, it is difficult to precisely measure the water content of a substance which is susceptible to oxidation at an elevated temperature.

SUMMARY OF THE INVENTION

It is, therefore, an object of the present invention to provide a simple device which can instantaneously measure a change in weight of a moisture-containing substance caused by the removal of the moisture.

Another object of the present invention is to provide a device of the above-mentioned type which can precisely measure the moisture content of an substance which is susceptible to oxidation by air.

It is an important object of the present invention to provide a device of the above-mentioned type in which the removal of the moisture is performed in an inert atmosphere.

In accomplishing the foregoing objects, there is provided in accordance with the present invention a device for measuring the moisture content of a moisture-containing substance, comprising:

an electronic balance for measuring and indicating the weight of a sample placed on a sample receiver thereof;

a sample holder for containing said moisture-containing substance, said sample holder defining an airtight chamber therewithin and having a bottom wall for receiving said moisture-containing substance thereon and a side wall upwardly extending from the periphery of said bottom wall, said sample holder being provided with a gas discharge pipe extending outwardly from said side wall so that said airtight chamber is in fluid communication with the outside of said sample holder only through said gas discharge pipe, and said sample holder being so shaped as to be held on said sample receiver of said electronic balance;

a gas feed tube having a first end for connection to a source of an inert gas and an open second end, said gas feed tube having a front portion adjacent to said second end which has an outside diameter smaller than the inside diameter of said gas discharge pipe, so that said front portion is adapted to be positioned in such a fixed position where said front portion is inserted into said gas discharge pipe to define an annular space between said gas discharge pipe and said front portion with said second end being located in said airtight chamber;

means for holding said front portion of said gas feed tube in said fixed position;

gas heating means for heating a flow of the inert gas in said gas feed tube; and sample heating means for heating said sample placed on said sample receiver, whereby when said sample holder containing said moisture-containing substance is placed as said sample on said sample receiver and when said first end of said gas feed tube is connected to said inert gas source with said front portion thereof being positioned in said fixed position, said moisture-containing substance is heated with said sample heating means in the atmosphere of said inert gas, so that the moisture of said moisture-containing substance is vaporized and liberated therefrom and is discharged together with said inert gas through said annular space from said airtight chamber and so that the change in weight of said moisture-containing substance caused by the loss of the moisture is detected by said electronic balance.

BRIEF DESCRIPTION OF THE DRAWINGS

Other objects, features and advantages of the present invention will become apparent from the detailed description of the invention which follows, when considered in light of the accompanying drawings in which.

DETAILED DESCRIPTION OF THE PREFERRED EMBODIMENT OF THE INVENTION

Figure 1:
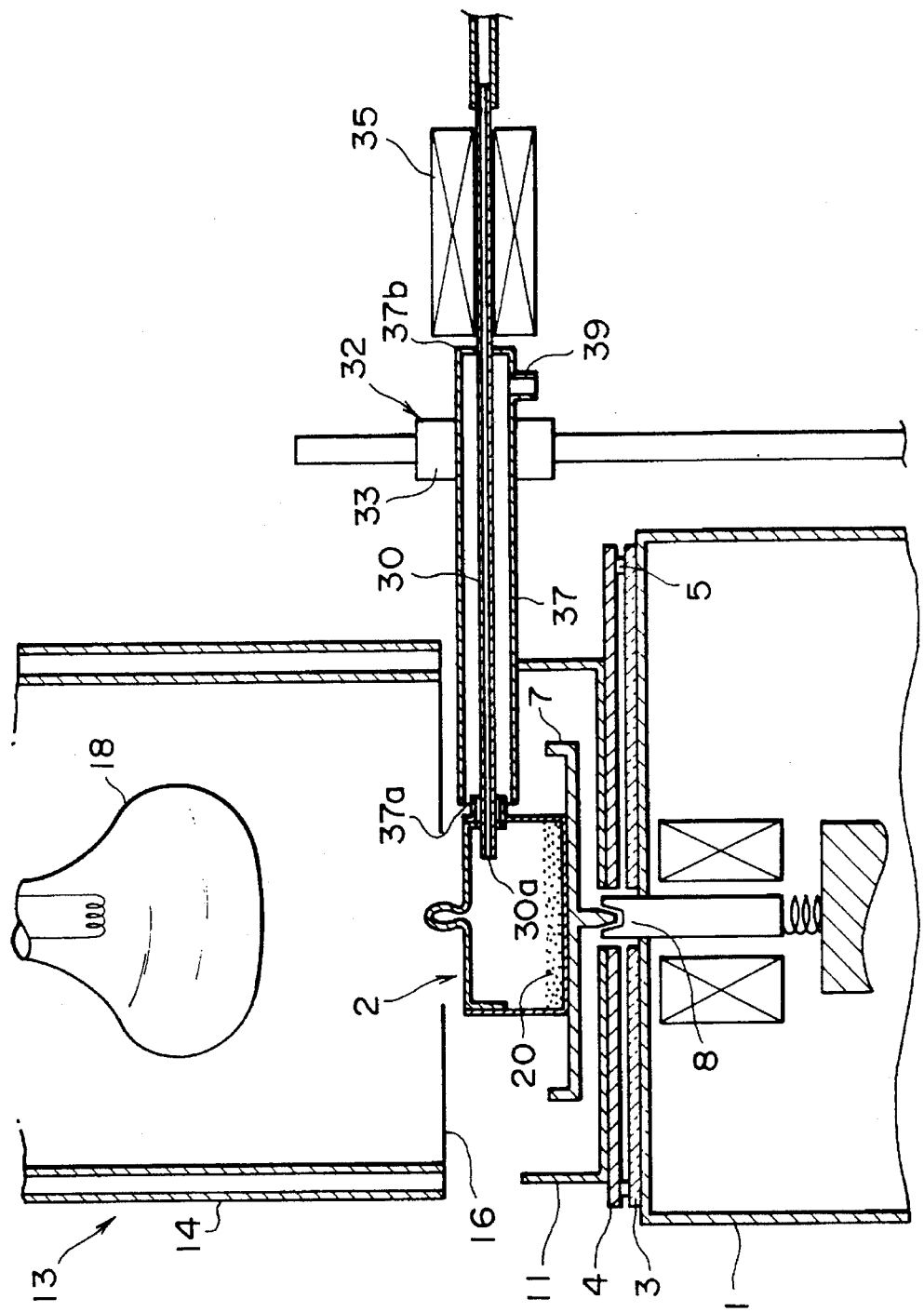
FIG. 1 is an elevational, cross-sectional view diagrammatically showing one embodiment of an aquameter according to the present invention.
Figure 2:
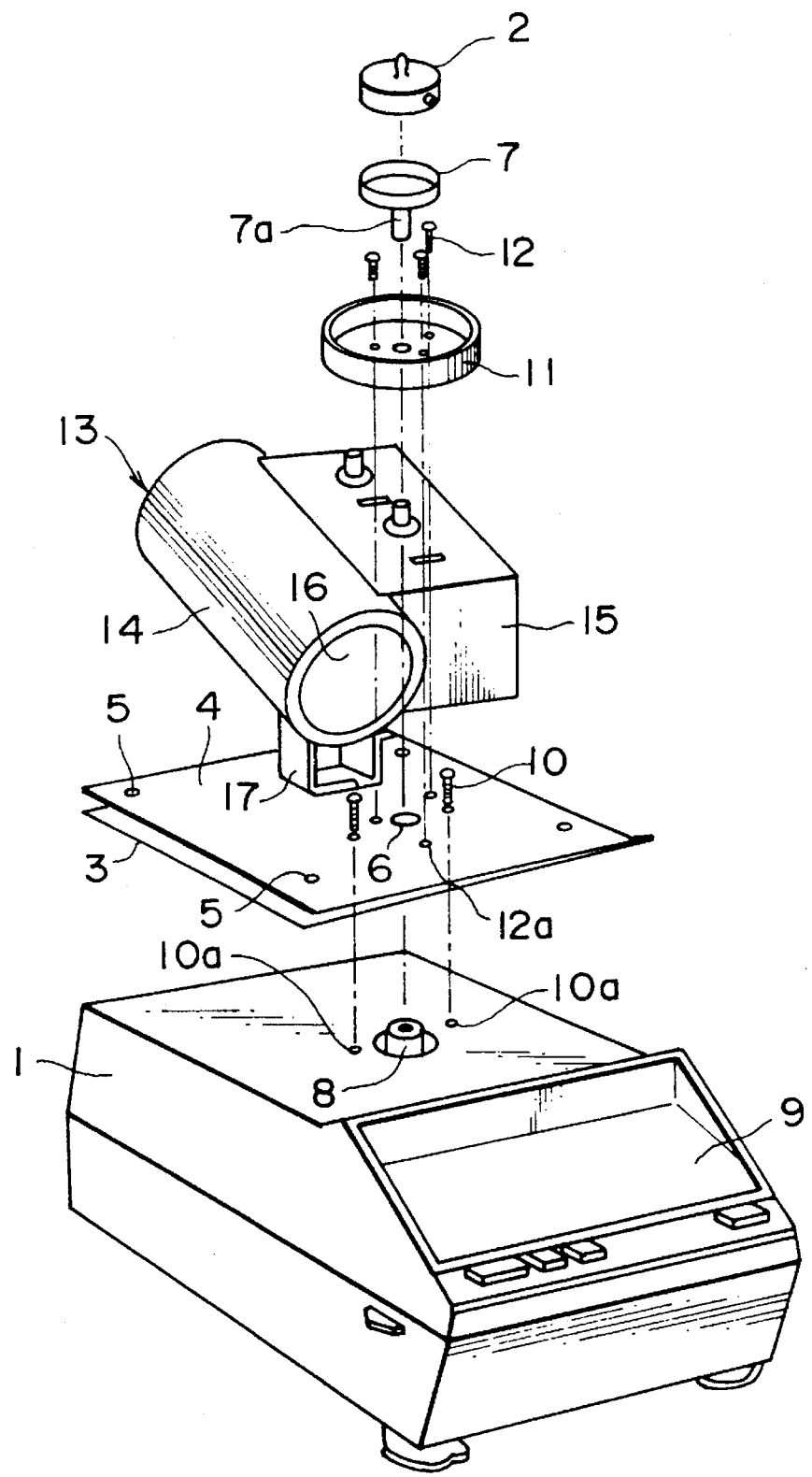
FIG. 2 is a partial, exploded, perspective view diagrammatically showing the structure of a heater and electronic balance assembly of the aquameter of FIG. 1.

Referring to FIGS. 1 and 2, designated as 1 is an electronic balance for measuring and indicating the weight of a sample holder 2 containing a water-containing substance 20 and placed on a sample receiver 7 thereof. The electronic balance has an upper surface overlaid with a heat-insulating plate 3 which, in turn, is covered with a metal plate 4. The metal plate 4 is fixedly secured by connecting members 5 to the insulating plate 3 with a small gap being defined therebetween to minimize the transmission of heat from the metal plate 4 to the insulating plate 3. The assembly of the plates 3 and 4 is fixed on the upper surface of the electronic balance 1 by screws 10 which are engageable with screw threads 10a of the electronic balance 1.

The plates 3 and 4 have central holes 6 through which a stem 7a of the sample receiver 7 is inserted for fitting engagement with an electromagnetic sensor section 8 of the electronic balance 1. The sample holder 2 is adapted to be held on the receiver 7 so that the weight of the water-containing substance 20 placed in the sample holder 2 is measured by the electronic balance 1 and is digitally indicated on a front indicating panel 9 thereof. Namely, when a vertical load is applied to the sensor section 8, a balancing force is electromagnetically acted thereon. The balancing force is converted into an electrical signal indicative of the load. An electronic balance of this type is well known per se and is commercially available. Any type of electronic balance may be suitably used for the purpose of the present invention as long as the sample receiver is of a type which does not vertically move during the weight measurement.

Designated as 11 is a wind shield fixed on the metal plate 4 by screws 12 engageable with screw threads 12a of the metal plate 4. The wind shield 11 serves to prevent a flow of air from acting on the sample holder 2 and to minimize the error of measurement attributed to the influence of the air flow.

Secured on the metal plate 4 is a heater assembly 13 for heating the sample 20 contained in the sample holder 2 placed on the receiver 7. The heater assembly has a cylindrical cover 14 with a lower open ended portion 16 and an infrared lamp 18 fixed within the cover 14. The cover 14 is hinged on the metal plate 4 through a supporting member 17 so that the cover 14 is able to be displaced between an open position as shown in FIG. 2 and a close position as shown in FIG. 1. In the close position, the cylindrical cover 14 is oriented in the direction normal to the surface of the metal plate 4 with the lower open end portion 16 being maintained in spaced apart from the metal plate 14. The reference numeral 15 shows an electrical control section for the infrared lamp 13.

Figure 3:
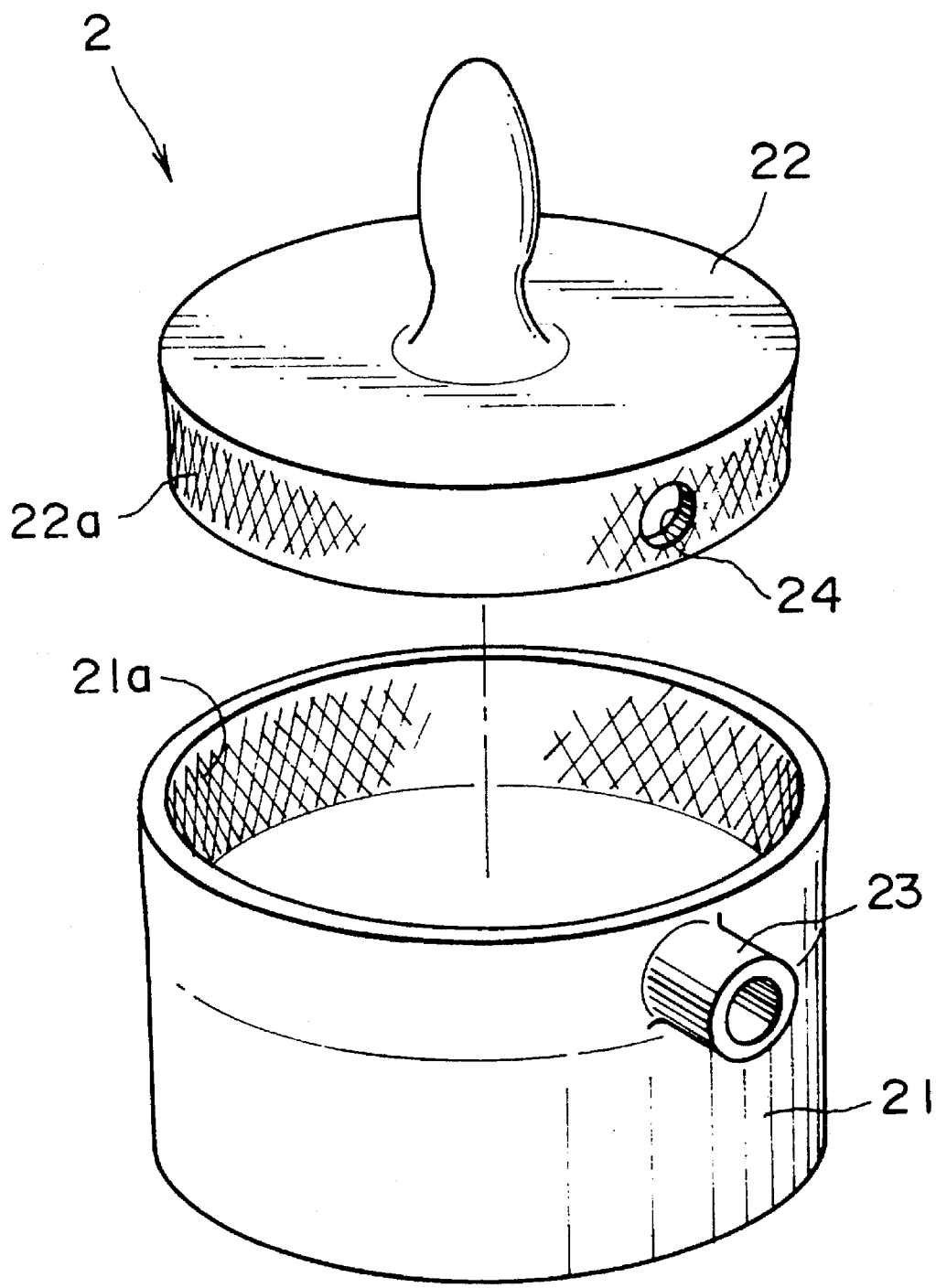
FIG. 3 is a perspective view schematically illustrating a sample holder of FIG. 1.

Referring to FIG. 3, the sample holder 2 of the illustrated embodiment is a heat-resistant glass vessel 21 having an open top end which is closed by a lid 22. The lid 22 has a ground outside surface 22a which is closely engageable with a ground inside surface 21a of the vessel 21 so that when the lid 22 is fitted into the vessel 21, there is defined an airtight chamber therebetween. The vessel 21 has a side wall provided with a gas discharge pipe 23 extending outwardly from the side wall so that the airtight chamber is in fluid communication with the outside of the vessel 21 only through the gas discharge pipe 23. The lid 22 is provided with an opening 24 at such a position as to match with the hole of the discharge pipe 23 when fitted to the vessel 21. It is preferred that the discharge pipe 23 be oriented horizontally when the sample holder 2 is placed on the sample receiver 7. The gas discharge pipe 23 generally has a length of 3–20 mm and an inside diameter of 3–10 mm.

Referring again to FIG. 1, a gas feed tube 30 extends through the gas discharge pipe 23 to define an annular space therebetween. The tube 30 has a first end connected to a source of an inert gas (not shown) and an open second end 30a. The gas feed tube 30 also has a front portion adjacent to the second end 30a which has an outside diameter smaller than the inside diameter of the gas discharge pipe 23, so that the front portion is adapted to be positioned in a fixed position, a horizontal position in the embodiment shown in FIG. 1, where the front portion is inserted into the gas discharge pipe 23 to define an annular space between the gas discharge pipe 23 and the front portion with the second end 30a being located in the airtight chamber. A metal tube is suitably used as the gas feed tube 30. The front portion of the gas feed tube 30 preferably has such an outer diameter as to define a gap of 1–3 mm between the inside surface of the gas discharge pipe 23 and the outer surface of the front portion of the tube 30.

Designated generally as 32 is means for holding the front portion of the gas feed tube 30 in the fixed position. Any conventionally known holding mechanism may be adopted for the purpose of the present invention as long as the tube 30 may be fixed in position. The holding means 32 in the illustrated embodiment includes a cramp mechanism 33 adapted to grasp the tube 30 and to be vertically and horizontally moved and rotated so that the position and orientation of the tube 30 secured by the cramp mechanism 33 can be suitably adjusted to prevent the front portion of the tube 30 inserted into the gas discharge pipe 23 from contacting with the inside wall of the gas discharge pipe 23.

For heating a flow of the inert gas in the gas feed tube 30, there is provided heating means 35 such as a sheath heater.

Preferably, the tube 30 is sheathed by an outer tubular member 37 to minimize the diffusion of outside air into the airtight chamber through the gas discharge pipe 23. The sheath 37 has an open end 37a and a closed end 37b and a fore portion adjacent to the open end 37a which has an inside diameter greater than the outer diameter of the gas discharge pipe 23 of the vessel 21. The sheath 37 is disposed such that the fore portion thereof surrounds the outer periphery of the gas discharge pipe 23 and part of the gas feed tube 30 extending outward from the gas discharge pipe 23. Designated as 39 is an evacuation port for connection to evacuating means (not shown). Thus, since the pressure inside of the airtight chamber is greater than that of the outside atmosphere adjacent to the open ended portion of the gas discharge pipe 23, the outside air is prevented from entering the gas discharge pipe 23. Further, the gas discharged from the gas discharge pipe 23 is withdrawn from the evacuation port and is prevented from escaping from the open end 37a of the sheath 37.

If desired, a thermocouple thermometer (not shown) may be provided for measuring the temperature within the airtight chamber. In this case, it is advantageous to use the gas feed tube 30 for supporting lead wires and a sensor of the thermometer. Preferably, the tube 30 is surrounded by a heat insulator to minimize the loss of heat of the inert gas flowing therethrough.

In measurement, the moisture-containing substance 20 is first placed within the sample holder 2. The holder is then placed on the receiver 7 of the electronic balance. The gas feed tube 30 is then inserted into the gas discharge pipe 23 of the sample holder 2. The position and the orientation of the tube 30 is adjusted so as to prevent the tube 30 from contacting with the discharge pipe 23. The cover 14 is then located over the sample holder 2. The inert gas is fed through the tube 30 to the inside of the sample holder 2 to substitute the air within the sample holder 2 with the inert gas. The heater 18 and the gas heating means 35 are energized to dry the sample 20 contained in the holder 2. Thus, the sample is heated, so that the moisture of the sample is vaporized and liberated therefrom. The liberated water is discharged from the sample holder 2 through the annular space between the discharge pipe 23 and the gas feed tube 30. When the gas discharge pipe 23 is oriented in a horizontal direction, the feed and discharge of the gas have little influence upon the precision of the measurement. The change in weight of the sample caused by the loss of the moisture is detected by the electronic balance 1.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What Is claimed Is:

1. A device for measuring the moisture content of a moisture-containing substance, comprising:

an electronic balance for measuring and indicating the weight of a sample placed on a sample receiver thereof;

a sample holder for containing said moisture-containing substance, said sample holder defining an airtight chamber therewithin and having a bottom wall for receiving said moisture-containing substance thereon and a side wall upwardly extending from the periphery of said bottom wall, said sample holder being provided with a gas discharge pipe extending outwardly from said side wall so that said airtight chamber is in fluid communication with the outside of said sample holder only through said gas discharge pipe, and said sample holder being so shaped as to be held on said sample receiver of said electronic balance;

a gas feed tube having a first end for connection to a source of an inert gas and an open second end, said gas feed tube having a front portion adjacent to said second end which has an outside diameter smaller than the inside diameter of said gas discharge pipe, so that said front portion is adapted to be positioned in such a fixed position where said front portion is inserted into said gas discharge pipe to define an annular space between said gas discharge pipe and said front portion with said second end being located in said airtight chamber;

means for holding said front portion of said gas feed tube in said fixed position;

gas heating means for heating a flow of the inert gas in said gas feed tube; and sample heating means for heating said sample placed on said sample receiver, whereby when said sample holder containing said moisture-containing substance is placed as said sample on said sample receiver and when said first end of said gas feed tube is connected to said inert gas source with said front portion thereof being positioned in said fixed position, said moisture-containing substance is heated with said sample heating means in the atmosphere of said inert gas, so that the moisture of said moisture-containing substance is vaporized and liberated therefrom and is discharged together with said inert gas through said annular space from said airtight cheer and so that the change in weight of said moisture-containing substance caused by the loss of the moisture is detected by said electronic balance.

2. A device as claimed in claim 1, further comprising an outer tubular member having an open end and a fore portion adjacent to said open end which has an inside diameter greater than the outer diameter of said gas discharge pipe of said sample holder, said tubular member being disposed such that said fore portion thereof surrounds the outer periphery of said gas discharge pipe and part of said gas feed tube extending outward from said gas discharge pipe, and said tubular member being provided with an evacuation port for connection to evacuating means so that the air within said outer tubular member is prevented from entering said airtight chamber through said air discharge pipe.

3. A device as claimed in claim 1, wherein said sample heating means includes an infrared lamp and said sample holder is formed of a heat-resistant glass.

4. A device as claimed in claim 1, wherein said gas discharge pipe extends in a substantially horizontal direction when said sample holder is held on said sample receiver.

* * * * *

UNITED STATES PATENT AND TRADEMARK OFFICE
CERTIFICATE OF CORRECTION

PATENT NO. : 5,499,532
DATED : March 19, 1996
INVENTOR(S) : KAIHO et al

It is certified that error appears in the above-indentified patent and that said Letters Patent is hereby corrected as shown below:

Col. 6, line 7, delete "cheer" and insert --chamber--.

Signed and Sealed this

Fifteenth Day of October, 1996

Attest:

BRUCE LEHMAN

*Attesting Officer*   *Commissioner of Patents and Trademarks*